United States Patent [19]

Schmieding et al.

[11] Patent Number: 5,466,243
[45] Date of Patent: Nov. 14, 1995

[54] METHOD AND APPARATUS FOR INSTALLING A SUTURE ANCHOR THROUGH A HOLLOW CANNULATED GRASPER

[75] Inventors: Reinhold Schmieding, Naples, Fla.; Stefan Krupp, Munich, Germany

[73] Assignee: Arthrex, Inc., Naples, Fla.

[21] Appl. No.: 197,829

[22] Filed: Feb. 17, 1994

[51] Int. Cl.⁶ .................................................. A61B 17/00
[52] U.S. Cl. ............................. 606/232; 606/60; 606/73; 606/104; 606/205
[58] Field of Search ..................... 606/205–208, 606/151, 148, 139, 232, 60, 65, 72, 73, 75, 104, 116, 117

[56] References Cited

U.S. PATENT DOCUMENTS

| | | | |
|---|---|---|---|
| 3,596,292 | 8/1971 | Erb et al. | 606/185 |
| 3,682,177 | 8/1972 | Ames et al. | 128/753 |
| 4,469,109 | 9/1984 | Mehl | 128/753 |
| 4,632,100 | 12/1986 | Somers et al. | 606/73 |
| 4,738,255 | 4/1988 | Goble et al. | 606/232 |
| 4,836,205 | 6/1989 | Barrett . | |
| 4,898,156 | 2/1990 | Gatturna et al. | 606/72 |
| 4,899,743 | 2/1990 | Nicholson et al. | 606/139 |
| 5,141,520 | 8/1992 | Goble et al. | 606/232 |
| 5,209,747 | 5/1993 | Knoepfler | 606/208 |
| 5,211,650 | 5/1993 | Noda | 606/148 |
| 5,217,468 | 6/1993 | Clement | 606/206 |
| 5,281,230 | 1/1994 | Heidmueller | 606/205 |
| 5,286,255 | 2/1994 | Weber | 606/205 |
| 5,312,432 | 5/1994 | Pingleton et al. | 606/205 |
| 5,370,662 | 12/1994 | Stone et al. | 606/73 |
| 5,372,604 | 12/1994 | Trott | 606/232 |

Primary Examiner—Stephen C. Pellegrino
Assistant Examiner—Jeffrey A. Schmidt
Attorney, Agent, or Firm—Ostrolenk, Faber, Gerb & Soffen

[57] ABSTRACT

An arthroscopic method and apparatus for implanting a suture fixation device or other appliance into tissue using a hollow cannulated grasper. Tissue at a repair site is secured with a hollow grasper. Suture material is appended to a suture anchor. The suture anchor or other appliance is attached to a device driver and installed through the hollow grasper into the repair site, where it is drilled into bone.

12 Claims, 2 Drawing Sheets

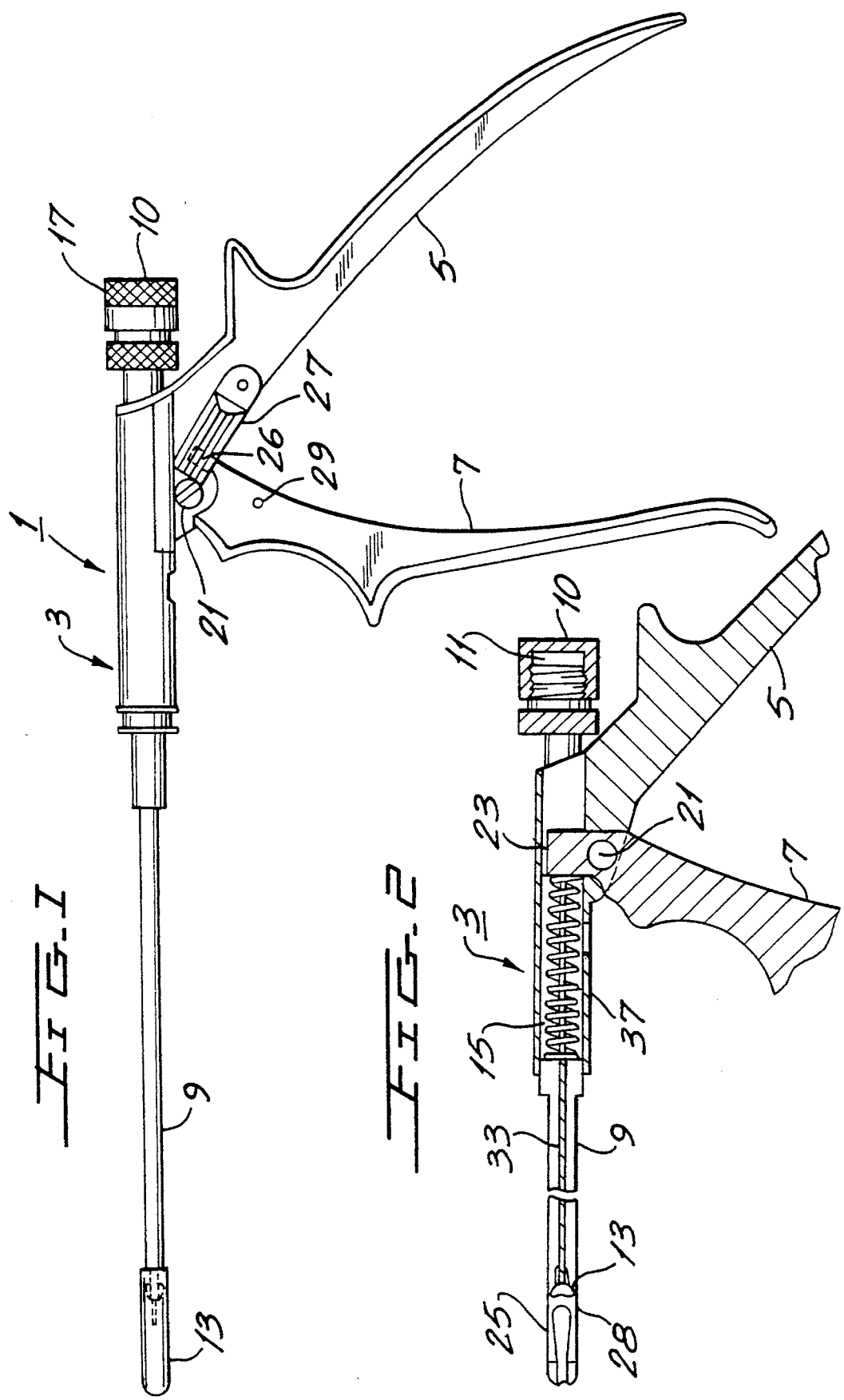

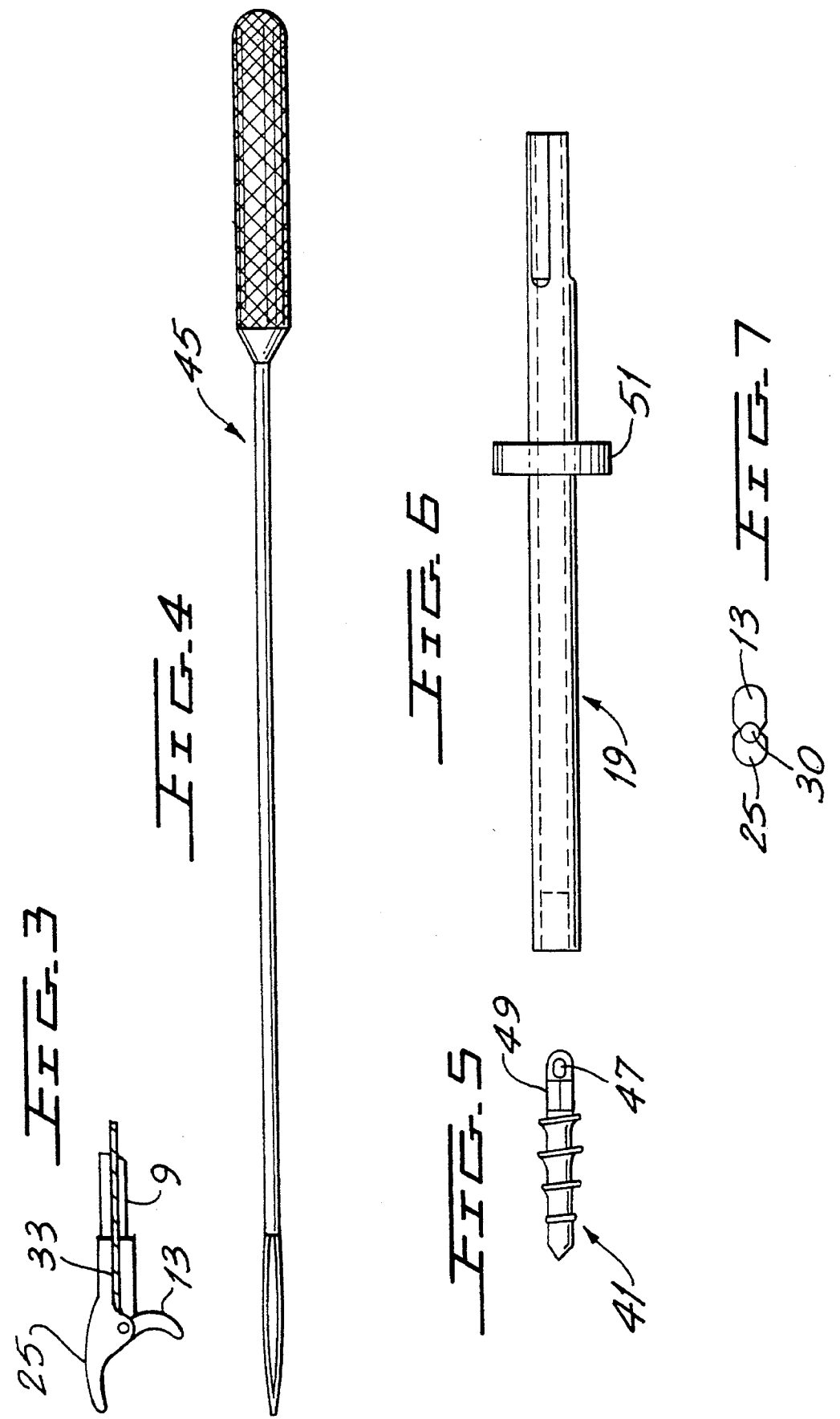

METHOD AND APPARATUS FOR INSTALLING A SUTURE ANCHOR THROUGH A HOLLOW CANNULATED GRASPER

BACKGROUND OF THE INVENTION

1. Field of the Invention

The present invention relates to an arthroscopic surgical method and apparatus for suture fixation, and specifically to an arthroscopic method and apparatus for installing a suture anchor through a hollow grasping means.

2. Brief Description of the Prior Art

Suture anchors are used in arthroscopic surgery to secure suture material to tissue. Various suture anchor assemblies have been developed. For example, U.S. Pat. Nos. 4,632,100 to Somers et al. and 4,898,156 to Gatturna et al. disclose suture anchors and tools for suture anchor installation. See also U.S. Pat. No. 4,899,743 to Nicholson et al.

The devices of the above-mentioned patents are disadvantageous because they do not secure the anchor-delivering end of the driver at the tissue repair site while the suture anchor is driven into the repair tissue. In order to provide stabilization at the tissue site, many of the prior art devices require that the suture anchor be inserted into a pre-drilled hole, as in Gatturna et al. and Nicholson et al. Other prior art devices, such as the device taught by Somers, rely on the technical skill of the surgeon to screw, for example, a self-tapping suture anchor into bone.

Guiding small suture anchor pins and driving them into bone tissue can be excessively demanding, particularly, for example, in arthroscopic Bankart repair. Inserting suture anchors into the glenoid rim is technically formidable, making the procedure infeasible.

SUMMARY OF THE INVENTION

The present invention overcomes the above-noted disadvantages by providing a method and apparatus for installing a suture anchor or other appliance through a hollow cannulated grasper. The grasper secures tissue at the installation site, providing a sturdy guide-way through which suture anchors and other appliances can be delivered to a tissue repair site for implantation.

The method of the present invention for installing a suture anchor includes the steps of grasping tissue with a hollow grasper and introducing a threaded suture anchor to the tissue through the hollow grasper. Once the suture anchor is implanted, the hollow grasper is removed, leaving the suture anchor in place.

The depth of implantation can be controlled with a depth gauge or drill stop device. The method is repeated to effect further suture anchor installations.

By the method of the present invention, arthroscopic implantation of suture anchors is made simpler and more feasible due to increased stability at the tissue site during installation.

Other features and advantages of the present invention will become apparent from the following description of the invention which refers to the accompanying drawings.

BRIEF DESCRIPTION OF THE DRAWINGS

FIG. 1 is a left side elevation perspective of a preferred hollow grasper device utilized in accordance with the method of the present invention.

FIG. 2 is a cut away detail of the grasper and jaw assembly.

FIG. 3 is a partial side view of the grasper showing the jaw assembly in an open position.

FIG. 4 is a left side elevation perspective of a suture material threading device used with the apparatus and method of the present invention.

FIG. 5 is an enlarged left side elevation perspective of a preferred suture anchor used with the apparatus and method of the present invention.

FIG. 6 is an enlarged left side elevation perspective of a preferred suture fixation device driver used with the apparatus and method of the present invention.

FIG. 7 is a partial end view of the present invention showing the jaw assembly in a closed position.

DETAILED DESCRIPTION OF THE PREFERRED EMBODIMENT

Referring to FIG. 1, the present invention relates to a hollow cannulated grasper 1 consisting of a handpiece 3 having a pistol grip 5, a trigger 7, an elongated, hollow barrel 9, a cap 10 encasing a fluid dam 11, and a moveable jaw 13.

As shown in FIG. 2, handpiece 3 includes a hollow portion 15. Cap 10, disposed at the back end of handpiece 3, includes knurls 17 on its outer surface which provide a grip for unscrewing the cap for removal of fluid dam 11 contained therein. Fluid dam 11 is formed of a replaceable, flexible material, such as rubber. A device driver 19 shown in FIG. 6, is designed to be pushed through a pair of cross-hatched slits (not shown) in the center of fluid dam 11. The rubber fits snugly around devices pushed through fluid dam 11 and inhibits back flow of body fluids during surgical procedures.

Trigger 7 is pivotally connected to the handpiece by pivot pin 21. The trigger 7 includes an extension 23 (FIG. 2) which projects into the hollow portion 15 of handpiece 3.

A barrel 9 is secured to the front end of handpiece 3. Barrel 9 includes a stationary jaw 25 disposed at its distal end. The distal end of barrel 9 also includes a moveable jaw 13 manipulated by the operator using trigger 7, as described in further detail below.

The grasper 1 is held in one hand using trigger 7 and pistol grip 5. The handpiece 3 can be grasped with the other hand to steady the instrument, if so desired.

Both the stationary jaw 25 and the moveable jaw 13 are provided with sharp tips 28 to assist in biting into the tissue. Tips 28 cooperate to form an opening 30, shown in FIG. 7, through which a suture anchor can pass when the jaws are closed.

In the operation of the device, the distal end of the grasper is positioned at the repair site against the tissue to be grasped. Moveable jaw 13 is advanced toward stationary jaw 25 by squeezing trigger 7 toward pistol grip 5. As trigger 7 moves inward by pivoting about pivot pin 21, extension 23 is urged against rod 33, advancing rod 33 forward toward the distal end of barrel 9 against the force of spring 37. When rod 33 is advanced forward, moveable jaw 13 pivots toward stationary jaw 25 to close the jaws. Once the appropriate section of tissue is isolated and grasped by jaws 13, 25, the trigger 7 may be locked in its closed position by rotating a latch 27 counterclockwise, such that a slot 26 in latch 27 is secured over a pin 29.

A threaded suture anchor 41 (FIG. 5) is then inserted through the device using device driver 19. To thread the suture anchor 41, appropriately sized suture is threaded through an eye 47 of suture anchor 41. Eye 47 and drive end 49 of suture anchor 41 are seated in device driver 19. Threading device 45 (FIG. 4) may be used to thread the suture through device driver 19.

Next, the threaded suture anchor and device driver are inserted through the fluid dam 11 of the cannulated grasper 1 and into the hollow barrel 9. When the device driver is fully inserted, the suture anchor 41 at the distal end thereof projects out through the end of the barrel and between the closed jaws into position at the tissue repair site.

A power drill is attached to the proximal end of driver 19. The suture anchor 41 is drilled through the closed jaws and into the repair site (e.g., the glenoid rim) in one maneuver. An adjustable drill depth guide stop 51 provides drilling depth control.

Once suture anchor 41 is in place, device driver 19 and cannulated grasper 1 are withdrawn from the repair site. The threaded suture anchor 41 is left in place for continuing the repair. Knots in the suture material may be tied using a knot pusher such as that described in U.S. Pat. No. 5,176,691. The installation procedure is repeated as necessary to install additional suture anchors.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for installing a suture anchor threaded with suture through tissue and into bone using a hollow grasping means, the method comprising the steps of:

(a) grasping the tissue with the hollow grasping means;
    (b) introducing the threaded suture anchor to the tissue through the hollow grasping means;
    (c) installing the threaded suture anchor through the tissue and into the bone; and
    (d) removing the hollow grasping means for the repair site, leaving the threaded suture anchor installed in the bone.

2. The method of claim 1, wherein the step of installing the threaded suture anchor comprises drilling the threaded suture anchor through the tissue and into the bone.

3. The method of claim 1, wherein the step of installing the threaded suture anchor through the tissue and into the bone comprises the steps of:

(a) coupling a proximal end of the threaded suture anchor to a device driver;
    (b) threading the suture from the threaded suture anchor through the device driver;
    (c) inserting the threaded device driver and the threaded suture anchor through the hollow grasping means;
    (d) attaching a power drill to the proximal end of the device driver; and
    (e) drilling the suture anchor through the tissue and into the bone.

4. The method of claim 1, further comprising the step of delivering the hollow grasping means to the tissue through a portal.

5. A surgical instrument set for grasping tissue and inserting a threaded suture anchor through tissue and into bone, comprising:

(a) a device driver comprising:
        (i) an elongated cannulated member having a distal end for receiving the suture anchor to be installed through the tissue and into the bone; and
        (ii) an adjustable depth stop disposed on said cannulated member for controlling the depth of installation of the suture anchor into the bone; and
    (b) a grasper/inserter instrument comprising:
        (i) a hollow handpiece having opposed front and back ends;
        (ii) an elongated hollow barrel secured to the front end of the handpiece, the barrel comprising a wall with a distal aperture, the wall of the barrel at the distal aperture extending to a stationary grasping means;
        (iii) an elongated rod movably disposed within the barrel, the rod having movable grasping means at a distal end thereof, the stationary and movable grasping means cooperating to grasp tissue; and
        (iv) hollow access means disposed on the back end of the handpiece for receiving the device driver, wherein, to implant the suture anchor into bone, the suture anchor is inserted into the distal end of the device driver, and the device driver is inserted, distal end first, into the back end of the handpiece of the grasper/inserter instrument, through the hollow access means and through the hollow barrel so that the suture anchor exits through the stationary and movable grasping means.

6. The surgical instrument set of claim 5, wherein the handpiece of the grasper/inserter instrument includes a pistol grip and a pivotally connected, spring-loaded trigger.

7. The surgical instrument set of claim 6, wherein the grasper/inserter instrument further comprises latching means mounted on the trigger and connectable to the pistol grip for securing the trigger in a closed position.

8. The surgical instrument set of claim 7, wherein an extension of the trigger of the grasper/inserter instrument extends into the hollow handpiece and cooperates with the rod to move the rod forward in the barrel when the trigger is pulled.

9. The surgical instrument set of claim 6, wherein the grasper/inserter instrument further comprises a spring disposed on the rod between the movable grasping means and a proximal end of the barrel, wherein when the trigger is pulled, the portion of the trigger within the handpiece pivots forward against the urging of the spring, moving the rod forward, such that the movable grasping means of the rod moves toward the stationary grasping means of the barrel in order to grasp tissue, whereby when the trigger is released, the portion of the trigger and rod are urged backward, and the trigger and the moveable jaw are urged into a normally open position.

10. The surgical instrument set of claim 5, wherein the hollow access means at the back end of the handpiece of the grasper/inserter instrument comprises a fluid dam.

11. The surgical instrument set of claim 10, wherein the fluid dam comprises resilient material removably retained within a screw cap.

12. The surgical instrument set of claim 6, wherein the elongated cannulated member of the device driver further comprises a proximal end for attachment to a power drill.

* * * * *